United States Patent [19]
Sandy

[11] 4,069,237
[45] Jan. 17, 1978

[54] PROCESS FOR MAKING TETRA (METHYL-ETHYL) LEAD COMPOUNDS

[75] Inventor: Charles Anthony Sandy, Wilmington, Del.

[73] Assignee: E. I. du Pont de Nemours and Company, Wilmington, Del.

[21] Appl. No.: 731,922

[22] Filed: Oct. 13, 1976

[51] Int. Cl.$^2$ .............................. C07F 7/26
[52] U.S. Cl. ................................ 260/437 R
[58] Field of Search ..................... 260/437 R

[56] References Cited

U.S. PATENT DOCUMENTS

| 2,270,108 | 1/1942 | Calingaert et al. | 260/437 R |
| 2,414,058 | 1/1947 | Pearsall | 260/437 R |

OTHER PUBLICATIONS

Tagliavini et al., Chemical Abstracts, 53, 1985/d, (1959).
Korshirnov et al., Chem. Abstracts, 54, 1298/b, (1960).

Primary Examiner—Helen M. S. Sneed
Attorney, Agent, or Firm—James A. Costello

[57] ABSTRACT

Tetraethyl lead is reacted with 0.5 to 4 moles of $CH_3X$ per mole of tetraethyl lead, in the presence of a catalytic amount of $AlY_3$, wherein X and Y are independently chloride, bromide, or iodide, at a temperature up to about 130° C, with the proviso that the reaction is conducted in the presence of an iodine-source selected from $AlI_3$, elemental iodine, $C_1$ to $C_4$ alkyl iodide and the like. The products are tetra(methyl-ethyl) lead redistribution compounds useful as fuel antiknocks.

10 Claims, No Drawings

PROCESS FOR MAKING TETRA (METHYL-ETHYL) LEAD COMPOUNDS

BACKGROUND OF THE INVENTION

1. Field of the Invention

This invention concerns a catalytic process for making tetra(methyl-ethyl) lead redistribution compounds which are useful as fuel antiknocks.

2. Description of the Prior Art

Heretofore, tetra(methyl-ethyl)lead redistribution compounds have been prepared according to processes characterized in that tetramethyl lead was a necessary reactant, either added as such or formed in situ. Representative of such prior art redistribution processes utilizing tetramethyl lead as a reactant are the following: contacting an alkali metal trialkyl plumbide with an alkylating agent in an aprotic medium according to U.S. Pat. No. 3,539,608; contacting sodium lead alloy, methyl chloride and tetraethyl lead in the presence of a catalyst according to U.S. Pat. No. 3,478,072; contacting at least two mixed alkyl lead compounds with a boron trifluoride alkyl etherate according to U.S. Pat. Nos. 3,151,141 and 3,151,142; contacting at least two mixed alkyl lead compounds with a silica-magnesia catalyst according to U.S. Pat. No. 3,527,780; and contacting alkyl lead compounds with organometallic halides or metal halides according to Calingaert et al. in J. Am. Chem. Soc. 61, 2748 ffg. and 3300 ffg. (1939).

A reaction known in the literature but one which does not produce redistribution products is disclosed by Korshunov et al. in J. Gen. Chem. (USSR) 39, 3100 (1959). In the disclosed reaction, tetraethyl lead is contacted with radioactive ethyl bromide in the presence of a catalyst such as $FeCl_3$, $AlBr_3$, $AlEt_3$ and $AlCl_3$. The reference process merely replaces some ethyl groups of the tetraethyl lead starting reactant with radioactive (thus traceable) ethyl groups from the ethyl bromide.

SUMMARY OF THE INVENTION

This invention concerns a process for preparing tetra(methyl-ethyl) lead redistribution compounds comprising reacting tetraethyl lead with about 0.5 to 4 moles of $CH_3X$ per mole of tetraethyl lead, in the presence of a catalytic amount of $AlY_3$, wherein X and Y are independently chloride, bromide or iodide, at a temperature up to about 130° C, with the proviso that the reaction is conducted in the presence of an iodine-source selected from $AlI_3$, elemental iodine, $C_1$ to $C_4$ alkyl iodide and the like.

By "redistributed", "lead redistribution" compounds, and "tetra(methyl-ethyl)lead" compounds is meant a mixture of five compounds, the proportion of each corresponding to a random (statistical) distribution of methyl and ethyl groups, as described more fully by Calingaert et al. in J. Am. Chem. Soc. 61, 2748 ffg. The five compounds are: tetramethyl lead, tetraethyl lead, monomethyltriethyl lead, dimethyldiethyl lead, and trimethylmonoethyl lead.

Concerning the proviso that iodine must be present during the reaction, it is pointed out that the amount necessary, expressed as iodide, is about 0.01 to 0.5 gram atom per mole of methyl halide in the reaction system. If X or Y is iodide, then a supplementary iodine-source is needed only to the extent that the requisite amount of iodine is not provided by said X or Y. Many iodine compounds can be used as sources of iodine as will be appreciated by those skilled in the art. Preferred iodine sources are $AlI_3$, elemental iodine and $C_1$ to $C_4$ alkyl iodides.

Preferred reaction temperatures are 20° to 125° C with most preferred temperatures being 80° to 120° C. Reactions at these temperatures are usually complete within a few minutes to 24 hours. Temperatures higher than about 130° C are generally to be avoided, particularly at long reaction times, to minimize thermal decomposition of the tetraalkyl lead compounds. No rigid lower temperature limit can be given. It is known, for instance, that certain combinations of reactants, such as methyl iodide, aluminum chloride, and tetraethyl lead undergo the exchange reaction at the relatively low temperature of −20° C. However, it cannot be said with certainty that all reactions will proceed at −20° C; or, if they do, that they will proceed speedily. Thus, temperatures lower than 20° C may be employed with the understanding that 20° C is the preferred low temperature. After the reaction is complete, the redistributed lead compounds are recovered by conventional techniques.

DETAILS OF THE INVENTION

In essence, the present process combines the process of an exchange of the methyl group of the methyl halide for the ethyl group of tetraethyl lead, with the process of redistributing methyl and ethyl groups to provide tetra(methylethyl) lead compounds. It is not known whether the exchange reaction and the redistribution reaction proceed step-wise or simultaneously.

A surprising aspect of this invention is the finding that if the methyl halide is methyl chloride or bromide and the aluminum halide is aluminum chloride or bromide, the exchange reaction will proceed not at all or only to an insignificant degree, i.e., less than 2% exchange of methyl groups for ethyl groups on the lead atom. Under such circumstances, the exchange reaction can be made to proceed by addition of a supplementary source of iodine as already explained.

The extent of exchange of the methyl groups of the methyl halide for the ethyl groups of the tetraethyl lead depends upon the particular molar ratio of methyl halide to tetraethyl lead employed, as will be appreciated by those skilled in the art. In the present specification, an exchange of, say 25%, indicates that 25% of the alkyl substituents of the tetra(methyl-ethyl) lead product will be methyl groups. Preferred tetra(methyl-ethyl)lead compounds are those wherein the methyl groups comprise about 10% to 90%, most preferably about 25% to 75% of the alkyl substituents. To produce such compounds, ratios of methyl halide to tetraethyl lead of 0.5 to 4, and preferably 1 to 3, are used.

The aluminum halide catalyst is used in the amount of about 0.05 to 0.1 mole, preferably about 0.075 to 0.085 mole, per mole of tetraethyl lead. Higher amounts of aluminum halide catalyst can be used if faster reaction rates are desired but generally higher concentrations are to be avoided to minimize the loss of tetraalkyl lead compounds.

The invention process is normally carried out neat; however, solvents can be used if desired. Included are aprotic polar solvents such as N,N-dimethylformamide, N,N-dimethylacetamide, N,N'-tetramethylurea and N,N',N"-hexamethylphosphoramide. Aprotic polar solvents enhance the exchange reaction particularly at temperatures above about 100° C. Preferred solvents are dimethylformamide and hexamethylphosphoramide, particularly the latter. When hexamethylphosphoramide is used, CAUTION must be exercised in view of speculation that it may be a carcinogen.

EXAMPLES

The following Examples illustrate the invention. In the Examples, hexamethylphosphoramide is referred to as HMPA; dimethylformamide as DMF; and tetramethyl urea as TMU.

The alkyl exchange reactions between methyl halides and tetraethyl lead were carried out in a 20 cc Parr Bomb modified to contain a ⅛ inch (3.175 mm) S/S Hoke valve (Hoke, Inc., Cresskill, NJ) in the bomb head. The bombs were oven-dried (100° C) overnight. Methyl halide, aluminum halide and tetraethyl lead (as well as a supplementary iodine compound and solvent when used) were charged into the bomb in the order listed. The charged bomb was heated in an oil bath with agitation at the designated temperature for the required reaction time. The reaction was terminated by immersing the bomb in a slurry of dry ice and acetone. The bomb was then placed in a water-ice bath and vented through the valve to remove gaseous by-products and volatile reactants.

After opening the bomb the reaction mixture was filtered free of solids and washed with 1% aqueous sodium hydroxide solution. The organolead phase was separated, dried over anhydrous calcium sulfate and analyzed by vapor phase chromatography. The gas chromatographic analysis of the reaction mixture was carried out in a F&M Model 720 Gas Chromatograph equipped with dual columns and linear temperature programming. The column was ¼ inch (6.35 mm) × 1½ meter nickel column packed with 60-80 mesh 12% neopentyl glycol sebacate on an acid-washed clay support (Chromosorb W). The sample size was 5 microliters and the column was temperature programmed at 10° C per minute (from 60° to 120° C). The eluting gas was helium at 60 ml/minute. Since alkyl exchange is accompanied by alkyl group redistribution, the extent of the exchange was calculated on the basis of the composition of the tetra(methyl-ethyl)lead redistribution products as determined by vapor phase chromatography. The calculation consists of determining the weight percent of each of the five compound: tetramethyl lead, tetraethyl lead, monomethyltriethyl lead, dimethyldiethyl lead, and trimethylmonoethyl lead; and then determining what percentage of the total of all alkyl groups are methyl groups. This percentage is expressed as percent exchange in the Examples.

EXAMPLES 1 TO 22

In these Examples the methyl halide reactant is methyl iodide. In each Example in Table 1, 4.95 g (15.3 m mole) of tetraethyl lead and 6.53 g (46 m mole) of methyl iodide were used unless indicated otherwise.

TABLE 1

METHYL IODIDE - TETRAETHYL LEAD SYSTEM

| Ex. | Reaction Temp. ° C | Hrs. | Catalyst AlY$_3$ | Grams | Solvent (grams) | Percent Exchange |
|---|---|---|---|---|---|---|
| 1 | 100 | 5 | AlCl$_3$ | 0.186 | — | 13 |
| 2 | 100 | 24 | AlBr$_3$ | 0.37 | — | 63.2 |
| 3 | 100 | 4 | AlBr$_3$ | 0.37 | — | 38.5 |
| 4 | 100 | 2 | AlBr$_3$ | 0.37 | — | 15.3 |
| 5 | 100 | 2 | AlBr$_3$ | 0.37 | HMPA (3.1) | 14.7 |
| 6 | 100 | 3 | AlBr$_3$ | 0.37 | — | 19.4 |
| 7 | 100 | 14 | AlBr$_3$ | 0.37 | — | 50.5 |
| 8 | 100 | 6 | AlBr$_3$ | 0.37 | — | 43.0 |
| 9 | 100 | 24 | AlI$_3$ | 0.57 | — | 45.3 |
| 10 | 120 | 4 | AlCl$_3$ | 0.186 | — | 62.5 |
| 11 | 120 | 0.5 | AlBr$_3$ | 0.18 | — | 13.9 |
| 12 | 120 | 1 | AlBr$_3$ | 0.18 | — | 20.4 |
| 13 | 120 | 4 | AlBr$_3$ | 0.37 | — | 40.8 |
| 14 | 120 | 8 | AlBr$_3$ | 0.37 | — | 58.8 |
| 15[1] | 120 | 4 | AlBr$_3$ | 0.37 | — | 59.1 |
| 16[2] | 120 | 4 | AlBr$_3$ | 0.37 | — | 63.5 |
| 17 | 120 | 4 | AlBr$_3$ | 0.50 | — | 57.5 |
| 18 | 120 | 4 | AlBr$_3$ | 0.20 | — | 11.1 |
| 18 | 120 | 4 | AlBr$_3$ | 0.20 | — | 11.1 |
| 19 | 120 | 4 | AlBr$_3$ | 0.27 | — | 32.1 |
| 20 | 120 | 1 | AlBr$_3$ | 0.37 | HMPA (3.1) | 45.3 |
| 21 | 120 | 4 | AlBr$_3$ | 0.37 | HMPA (3.1) | 72.0 |
| 22 | 120 | 0.5 | AlBr$_3$ | 0.37 | HMPA (3.1) | 19.3 |

Notes:
[1] 8.69 g (61.2 m mole) of methyl iodide
[2] 10.86 g (76.5 m mole) of methyl iodide

EXAMPLES 23 TO 40 AND COMPARISONS A TO I

In these Examples the methyl halide is methyl bromide. In each Example 4.95 g (15.3 m mole) of tetraethyl lead and 5.8 g (61 m mole) of methyl bromide was used unless indicated otherwise. The Examples in Table 2 show that little or no exchange takes place with aluminum chloride (Comparative Examples A and F) or aluminum bromide (Comparative Examples B, C, D, E, and G) as the catalyst. Appreciable exchange takes place only when iodine is present in the system, either as aluminum iodide catalyst or as iodine (Examples 28 and 29).

TABLE 2

METHYL BROMIDE - TETRAETHYL LEAD SYSTEM

| Example | Reaction Temp. ° C | Hrs. | Catalyst AlY$_3$ | Amt. | Iodine Source (grams) | Solvent (grams) | Percent Exchange |
|---|---|---|---|---|---|---|---|
| Comp. A | 100 | 4 | AlCl$_3$ | 0.186 | — | — | None |
| Comp. B | 100 | 4 | AlBr$_3$ | 0.37 | — | — | 0.1 |
| Comp. C | 100 | 24 | AlBr$_3$ | 0.37 | — | — | Trace |
| Comp. D | 100 | 4 | AlBr$_3$ | 0.37 | — | Glyme (4.3) | None |
| Comp. E | 100 | 2 | AlBr$_3$ | 0.37 | — | HMPA (3.1) | 2.0 |
| 23 | 100 | 24 | AlI$_3$ | 0.57 | — | — | 7.3 |
| 24 | 100 | 4 | AlI$_3$ | 0.57 | — | — | 0.7 |
| 25 | 100 | 24 | AlI$_3$ | 0.57 | — | DMF (9.5) | 41.4 |
| 26 | 100 | 24 | AlI$_3$ | 0.57 | — | HMPA (3.1) | 42.3 |
| 27 | 100 | 4 | AlI$_3$ | 0.57 | — | HMPA (3.1) | 19.1 |
| Comp. F | 120 | 4 | AlCl$_3$ | 0.186 | — | — | None |
| Comp. G | 120 | 4 | AlBr$_3$ | 0.37 | — | — | None |
| 28 | 120 | 4 | AlBr$_3$ | 0.5 | I$_2$ (0.53) | HMPA (4.1) | 36.9 |
| 29 | 120 | 4 | AlBr$_3$ | 0.37 | I$_2$ (0.53) | HMPA (4.1) | 26.3 |
| 30 | 120 | 4 | AlI$_3$ | 0.57 | — | — | 3.9 |
| 31 | 120 | 10 | AlI$_3$ | 0.57 | — | — | 6.4 |
| 32 | 120 | 4 | AlI$_3$ | 0.57 | — | — | 3.6 |
| 33 | 120 | 7 | AlI$_3$ | 0.57 | — | — | 4.0 |
| 34 | 120 | 10 | AlI$_3$ | 0.57 | — | — | 8.0 |
| 35 | 120 | 2 | AlI$_3$ | 0.57 | — | — | 2.4 |
| 36 | 120 | 7 | AlI$_3$ | 0.57 | — | HMPA (3.1) | 35.7 |

TABLE 2-continued

| | METHYL BROMIDE - TETRAETHYL LEAD SYSTEM | | | | | | |
|---|---|---|---|---|---|---|---|
| | Reaction | | | | | | |
| | Temp. | | Catalyst | | Iodine | | Percent |
| Example | °C | Hrs. | AlY$_3$ | Amt. | Source (grams) | Solvent (grams) | Exchange |
| 37 | 120 | 2 | AlI$_3$ | 0.57 | — | HMPA (3.1) | 6.4 |
| 38 | 120 | 10 | AlI$_3$ | 0.57 | — | HMPA (3.1) | 68.1 |
| 39[1] | 120 | 4 | AlI$_3$ | 0.57 | — | HMPA (3.1) | 17.2 |
| 40 | 120 | 4 | AlI$_3$ | 0.57 | — | TMU (3.0) | 6.9 |
| Comp. H | 120 | 4 | None | — | — | HMPA (3.1) | Trace |
| Comp. I | 100 | 2 | None | — | — | TMU (3.0) | Trace |

Notes:
[1]7.3 g (76.8 m mole) of methyl bromide

EXAMPLES 41 TO 63 AND COMPARISONS J TO L

In these Examples the methyl halide is methyl chloride. In each Example, 4.95 g (15.3 m mole) of tetraethyl lead was used unless indicated otherwise. The amount of methyl chloride used in each Example is indicated. Table 3 shows that when the methyl halide is methyl chloride, little or no exchange takes place with either aluminum chloride or aluminum bromide as the catalyst (Comparative Examples J, K, and L). However, the exchange reaction readily takes place when iodine is present in the system either in the form of aluminum iodide catalyst or elemental iodine or ethyl iodide (EtI) or combinations thereof.

TABLE 3

| | | METHYL CHLORIDE - TETRAETHYL LEAD SYSTEM | | | | | | |
|---|---|---|---|---|---|---|---|---|
| | | Reaction | | | | | | |
| | CH$_3$Cl | Temp. | | Catalyst | | Iodine | | Percent |
| Example | (g) | °C | Hrs. | AlY$_3$ | Amt. | Source (grams) | Solvent (grams) | Exchange |
| Comp. J | 3.5 | 100 | 4 | AlCl$_3$ | 0.186 | — | — | None |
| Comp. K | 3.5 | 100 | 24 | AlBr$_3$ | 0.37 | — | — | 0.3 |
| 41 | 4.5 | 100 | 8 | AlBr$_3$ | 0.50 | I$_3$ (0.53) | HMPA (4.0) | 15.1 |
| 42 | 3.5 | 100 | 24 | AlI$_3$ | 0.57 | — | — | 6.1 |
| 43 | 3.5 | 100 | 24 | AlI$_3$ | 0.57 | — | HMPA (3.1) | 7.9 |
| Comp. L | 3.5 | 120 | 4 | AlCl$_3$ | 0.186 | — | — | None |
| 44 | 4.5 | 120 | 2 | AlBr$_3$ | 0.50 | I$_3$ (0.53) | HMPA (4.0) | 10.1 |
| 45 | 4.5 | 120 | 4 | AlBr$_3$ | 0.50 | I$_2$ (0.53) | HMPA (4.0) | 21.4 |
| 46 | 4.5 | 120 | 6 | AlBr$_3$ | 0.50 | I$_2$ (0.53) | HMPA (4.0) | 27.2 |
| 47 | 3.5 | 120 | 4 | AlI$_3$ | 0.57 | — | — | 2.3 |
| 48 | 3.0 | 120 | 4 | AlI$_3$ | 0.78 | — | — | 5.5 |
| 49 | 3.0 | 120 | 4 | AlI$_3$ | 0.78 | — | HMPA (3.1) | 17.8 |
| 50 | 3.5 | 120 | 4 | AlI$_3$ | 0.57 | — | HMPA (3.1) | 4.8 |
| 51 | 4.5 | 120 | 4 | AlI$_3$ | 0.57 | I$_2$ (0.53) | HMPA (4.0) | 16.1 |
| 52 | 4.5 | 120 | 4 | AlI$_3$ | 0.78 | I$_2$ (0.53) | HMPA (4.0) | 32.1 |
| 53 | 3.0 | 120 | 4 | AlI$_3$ | 0.78 | I$_2$ (0.27) | HMPA (3.1) | 35.1 |
| 54 | 3.0 | 120 | 4 | AlI$_3$ | 0.78 | I$_2$ (0.40) | HMPA (3.1) | 48.3 |
| 55 | 3.0 | 120 | 4 | AlI$_3$ | 0.78 | EtI (0.12) | HMPA (3.1) | 51.6 |
| 56[1] | 2.1 | 120 | 1 | AlCl$_3$ | 0.1 | EtI (3.1) | HMPA (1.8) | 26 |
| 57[1] | 2.1 | 120 | 1.5 | AlCl$_3$ | 0.1 | EtI (3.1) | HMPA (1.8) | 33 |
| 58[1] | 2.1 | 120 | 2 | AlCl$_3$ | 0.1 | EtI (3.1) | HMPA (1.8) | 50 |
| 59[1] | 2.1 | 120 | 1 | AlCl$_3$ | 0.1 | EtI (6.4) | HMPA (1.8) | 6 |
| 60[1] | 2.1 | 120 | 1 | AlCl$_3$ | 0.1 | EtI (6.4) | — | 2 |
| 61[2] | 1.1 | 120 | 1 | AlCl$_3$ | 0.05 | EtI (3.1) | HMPA (1.8) | 21 |
| 62[2] | 1.1 | 120 | 2 | AlCl$_3$ | 0.05 | EtI (3.1) | HMPA (1.8) | 50 |
| 63[1] | 2.1 | 120 | 1 | AlBr$_3$ | 0.2 | EtI (3.1) | HMPA (1.8) | 37 |

Notes:
[1]3.1 g of tetraethyl lead
[2]1.6 g of tetraethyl lead

The embodiments of the invention in which an exclusive property or privilege is claimed are defined as follows:

1. A process for preparing tetra(methyl-ethyl) lead redistribution compounds comprising reacting tetraethyl lead with about 0.5 to 4 moles of CH$_3$X per mole of tetraethyl lead, in the presence of a catalytic amount of AlY$_3$, wherein X and Y are independently chloride, bromide or iodide, at a temperature up to about 130° C, with the proviso that the reaction is conducted in the presence of an iodine-source selected from AlI$_3$, elemental iodine or C$_1$ to C$_4$ alkyl iodide.

2. A process according to claim 1 wherein the iodine-source is AlI$_3$.

3. A process according to claim 1 wherein the iodine-source is elemental iodine.

4. A process according to claim 1 wherein the iodine-source is C$_1$ to C$_4$ alkyl iodide.

5. A process according to claim 4 wherein the alkyl iodide is CH$_3$I.

6. A process according to claim 1 comprising reacting the tetraethyl lead and CH$_3$X in an aprotic polar solvent.

7. A process according to claim 2 comprising reacting the tetraethyl lead and CH$_3$X in an aprotic polar solvent selected from N,N-dimethylformamide, N,N-dimethylacetamide, N,N'-tetramethylurea, and N,N',N''-hexamethylphosphoramide.

8. A process according to claim 3 comprising reacting the tetraethyl lead and CH$_3$X in an aprotic polar solvent selected from N,N-dimethylformamide, N,N-dimethylacetamide, N,N'-tetramethylurea, and N,N',N''-hexamethylphosphoramide.

9. A process according to claim 4 comprising reacting the tetraethyl lead and CH$_3$X in an aprotic polar solvent selected from N,N-dimethylformamide, N,N-dimethylacetamide, N,N'-tetramethylurea, and N,N',N''-hexamethylphosphoramide.

10. A process according to claim 5 comprising reacting the tetraethyl lead and CH$_3$X in an aprotic polar solvent selected from N,N-dimethylformamide, N,N-dimethylacetamide, N,N'-tetramethylurea, and N,N',N''-hexamethylphosphoramide.

* * * * *